United States Patent [19]

Payne et al.

[11] Patent Number: 4,515,475
[45] Date of Patent: May 7, 1985

[54] MEASUREMENT OF REFRACTIVE INDEX PROFILE

[75] Inventors: David N. Payne; Issei Sasaki; Michael J. Adams, all of Southampton, England

[73] Assignee: National Research Development Corporation, London, England

[21] Appl. No.: 308,542
[22] PCT Filed: Mar. 11, 1981
[86] PCT No.: PCT/GB81/00040
§ 371 Date: Oct. 1, 1981
§ 102(e) Date: Oct. 1, 1981
[87] PCT Pub. No.: WO81/02634
PCT Pub. Date: Sep. 17, 1981

[30] Foreign Application Priority Data

Mar. 11, 1980 [GB] United Kingdom ............... 8008158

[51] Int. Cl.$^3$ ............................................. G01N 21/47
[52] U.S. Cl. ..................................... 356/73.1; 356/128
[58] Field of Search ..................... 356/73.1, 124, 125, 356/126, 127, 128; 350/162.12

[56] References Cited

U.S. PATENT DOCUMENTS 3,870,415  3/1975  Cornsweet ........................ 356/124
4,168,907  9/1979  Presby .............................. 356/73.1
4,181,433  1/1980  Marcuse ........................... 356/73.1
4,348,108  9/1982  Shindow ........................... 356/125

OTHER PUBLICATIONS

Nondestructive Measurement of Index Profile of an Optical-Fibre Preform, Electronics Letters, vol. 13, No. 24, Nov. 24, 1977, pp. 736 and 738.
Refractive Index Determination by the Focusing Method, Applied Optics, D. Marcuse, vol. 18, No. 1, Jan. 1, 1979, pp. 9-12.
Optical Fiber Preform Diagnostics, H. M. Presby and D. Marcuse, Applied Optics, vol. 18, No. 1, Jan. 1, 1979, pp. 23-30.
Preform Index Profiling (PIP), H. M. Presby and D. Marcuse, Applied Optics, vol. 18, No. 5, Mar. 1, 1979, pp. 671-677.
Laser Beam Refraction Traversely Through a Graded-Index Preform to Determine Refractive Index Ratio and Gradient Profile, L. S. Watkins, Applied Optics, vol. 18, No. 13, Jul. 1, 1979, pp. 2214-2222.
Optical Method for Measuring the Radial Distribution of the Refractive Index, Ostrovskaya and Filippov, Soviet Physics Technical Physics, vol. 23, No. 11, published Nov. 1978 by America Institute of Physics, pp. 1364-1365.
Refractive Index Profile Determination of Optic Fibers from the Diffraction Pattern, Ernst Brinkmeyer, Applied Optics, vol. 16, No. 11, Nov. 1977, pp. 2802-2803.
Focusing Method for Nondestructive Measurement of Optical Fiber Index Profiles, D. Marcuse and H. M. Presby, Applied Optics, vol. 18, No. 1, Jan. 1, 1979, pp. 14-22.

Primary Examiner—R. A. Rosenberger
Attorney, Agent, or Firm—Cushman, Darby & Cushman

[57] ABSTRACT

A method of sensing the optical deflection function of an approximately cylindrical object, such as an optical fibre preform, comprises illuminating the object with collimated light; focusing the transmitted light so that in the focal plane the distance of the light from the optical axis is linearly proportional to the angle through which light has been deviated by the object; optically modulating the focused light so that a property of the light varies as a function of said distance, and calculating the deflection function from the modulated light. The modulations may be spatial or temporal. The refractive index profile can also be calculated.

15 Claims, 6 Drawing Figures

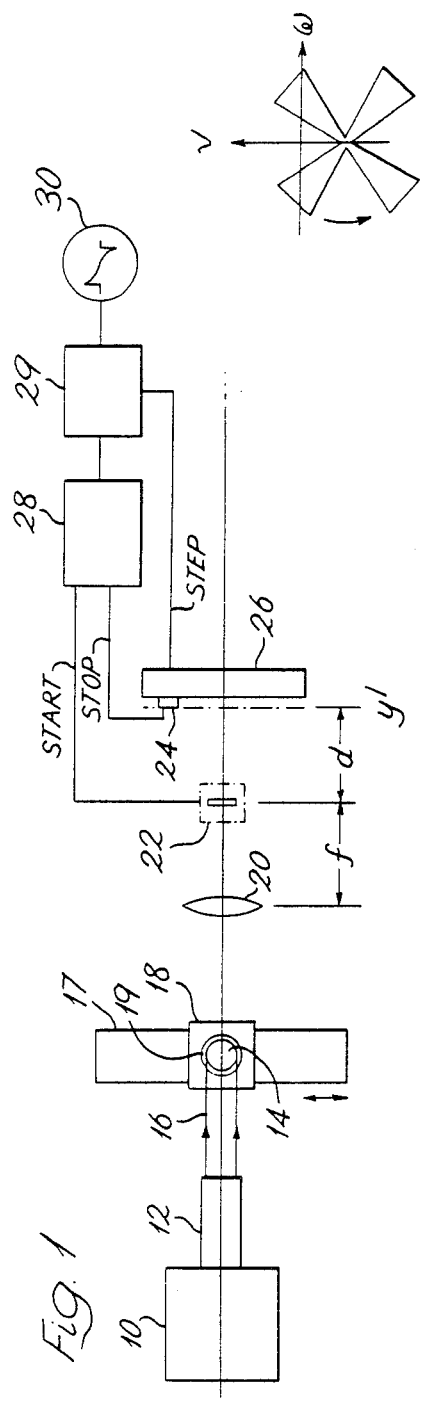
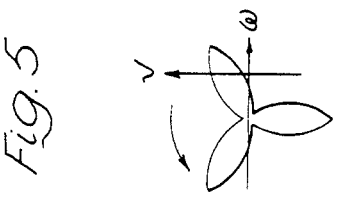
Fig. 5
Fig. 6
Fig. 1
Fig. 2

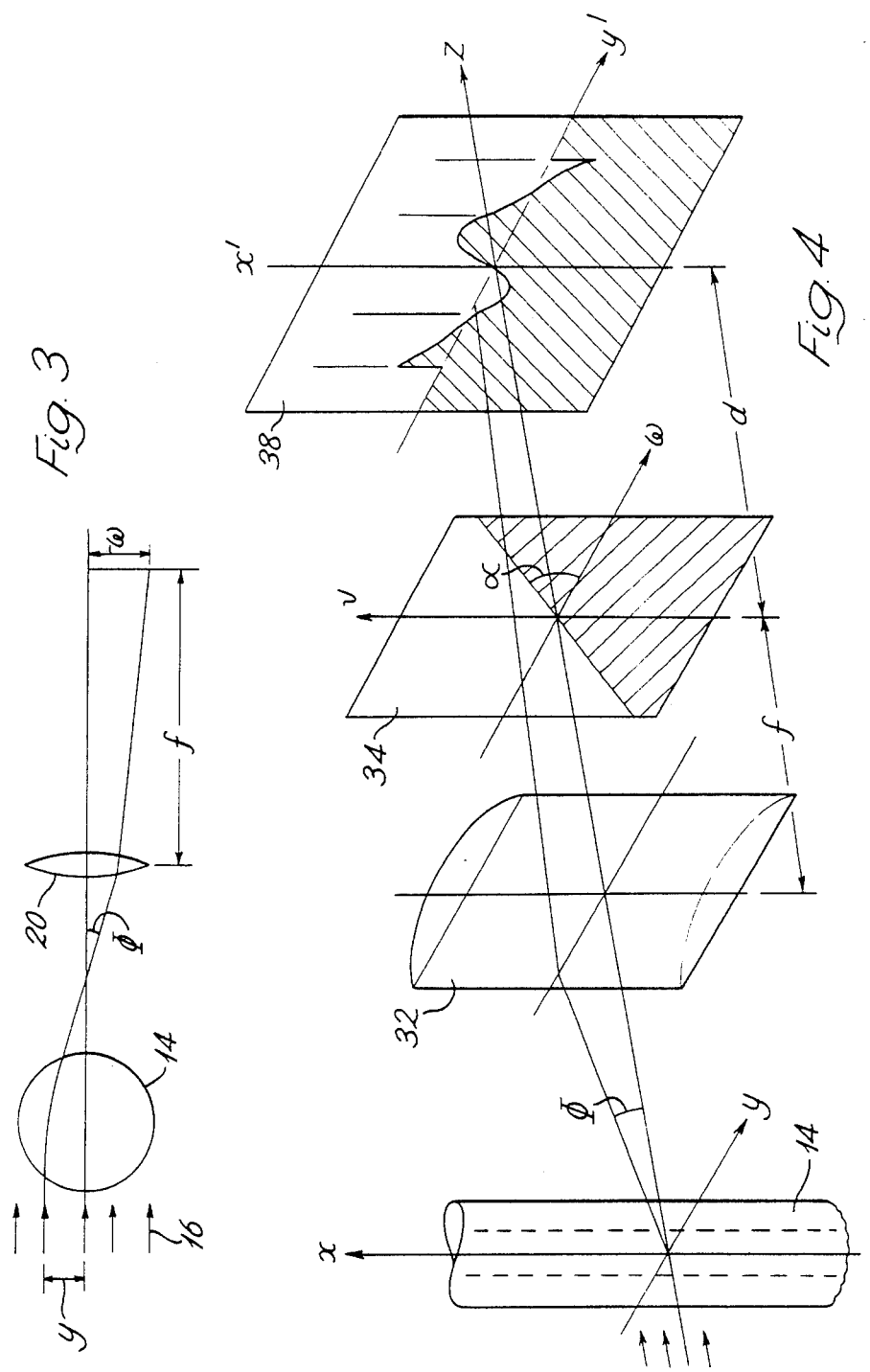

MEASUREMENT OF REFRACTIVE INDEX PROFILE

This invention concerns the measurement of refractive index profile across an object which is approximately cylindrical, such as an optical fibre, or an optical fibre preform, the measurement being made transverse to the cylindrical axis. Such objects ideally have circular symmetry and are invariant to the axial direction, but in practice major variations from the ideal conditions occur. Application of the present invention allows the variations to be sensed and quantified.

In this specification the term 'light' means electromagnetic radiation at visible, ultraviolet and infrared wavelengths.

In Electronics Letters Nov. 24, 1977, volume 13, No. 24, pages 736 to 738, P. L. Chu describes a method of measuring the refractive index profile of an optical fibre preform by scanning a laser beam of very small diameter across the preform in the radial direction, i.e. transverse to the cylindrical axis of the preform, and sensing the deflection of the output beam as a function of radial position of the input beam. The deflection function measured in this way is numerically transformed to determine the refractive index profile. This method requires an input beam of very small diameter, which may be difficult to achieve, and use of a laser introduces spurious interference patterns which may be difficult to eliminate.

In another method described by H. M. Presby and D. Marcuse in Applied Optics, Mar. 1, 1979, Volume 18, No. 5, pages 671 to 677, an optical fibre preform is illuminated uniformly across its diameter and the intensity distribution of the transmitted light is sensed; the deflection function is determined by a first mathematical integration and the refractive index profile is then determined by a second integration. In this method to achieve high accuracy it is essential to provide an illuminating beam which has a precisely uniform intensity distribution across the radius or diameter of the fibre, and an intensity sensing arrangement which has a precisely uniform response in this direction. Another difficulty is that strict validity of the theory requires the plane in which intensity is observed to be placed at a distance from the preform which is large compared to its radius; in practice the plane in which intensity is observed must be close to the preform to eliminate the effect of cross or superimposition of beams transmitted through different sections or through opposite halves of the preform so that a single-valued output is achieved.

The object of the present invention is to provide an improved method of sensing the deflection function of a cylindrical object.

According to the invention, a method of sensing the optical deflection function of an approximately cylindrical object comprises:

illuminating the object over its width to be tested with a collimated beam of light;

focusing the light transmitted by the object so that in the focal plane the distance of transmitted light from the optical axis in a direction perpendicular to the cylindrical axis of the object is linearly proportional to the angle through which light has been deviated by the object;

optically modulating the focused light so that a property of the light varies as a function of said distance; and receiving the modulated light in an image plane, whereby the deflection function of the object can be derived.

The focused light may be modulated so that either a temporal or a spatial property of the light varies in a direction parallel to said direction. In a temporal modulation, the light is pulsed, and the pulse width or pulse phase varies in said direction. In a spatial modulation, the intensity or the shadow height of the modulated light varies with said distance.

From the light received in the image plane an electrical signal related to the deflection function can be derived, and usually this signal will be mathematically transformed according to a known formula to derive the radial refractive index distribution of the object, i.e. the refractive index profile.

Also according to the invention, apparatus for sensing the optical deflection function of an approximately cylindrical object comprising in series array optical focusing means, optical modulating means, optical receiving means, and calculating means, arranged so that when the object is illuminated by a beam of collimated light, the receiving means receives light having a modulation which varies along a direction perpendicular to the optical axis of the apparatus and to the cylindrical axis of the object, said varying modulation indicating the angle through which light has been deviated by the object, and the calculating means calculating from said varying modulation the optical deflection function of the object.

In a first major embodiment the transmitted light is focused by a spherical lens, and the focused light is temporally modulated by repetitive movement of a shutter in the focal plane parallel to said radial direction, the time which elapses between start of a shutter sweep and the time the shutter extinguishes light received at any position in the image plane displaced from the optical axis in a direction parallel to said radial direction varying in accordance with the deflection function.

The shutter may be a rotary chopper blade, or alternatively, the shutter may vibrate linearly, for example when a shutter blade is attached to a resonating tuning fork.

In an alternative arrangement for applying a temporal modulation, a shutter is provided with repetitive movement in the focal plane perpendicular to said radial direction, the mark-space ratio of said shutter varying as a function of distance in the focal plane from the optical axis. The shutter will usually be a conventional rotary chopper having curved blade edges. In this arrangement the mark-space ratio of the transmitted light at any position in the image plane displaced from the optical axis in a direction parallel to said radial direction varies in accordance with the deflection function.

In a second major embodiment the light transmitted by the object is focused by a spherical lens and the focused light is spatially modulated by a filter having a transmittance which varies in the focal plane in a direction parallel to said radial direction. The intensity of the transmitted light at any point in the image plane displaced from the optical axis in a direction parallel to said radial direction provides an indication of the deflection suffered by the ray present at that point.

In an alternative arrangement for applying a spatial modulation, the transmitted light is focused by means of a cylindrical lens, arranged with its cylindrical axis parallel to the cylindrical axis of the object, and the focused light is spatially modulated by a knife edge in the focal plane, whereby a shadowgraph is produced in the image plane in which the shadow boundary corresponds to the deflection function of the object.

The knife edge may be straight and arranged to lie at an angle to both said orthogonal axes in the focal plane, alteration of said angle altering the magnitude of the shadowgraph co-ordinate in the direction parallel to the cylindrical axis of the object. Alternatively, the knife edge may be curved, such as "s" shaped or circular, in which case the shadowgraph will be related to the deflection function according to the known mathematical form of the knife edge.

The invention will now be described by way of example with reference to the accompanying drawings in which:

FIGS. 1 and 2 illustrate apparatus for sensing refractive index profile of an optical fibre preform using respectively temporal and spatial coding;

FIG. 3 is a ray diagram of part of FIG. 1;

FIG. 4 is a ray diagram of part of FIG. 2 showing the production of a shadowgraph, and FIGS. 5 and 6 show two forms of rotary chopper for temporal modulation.

FIG. 1 is a view from above and FIG. 2 is a side view of two different embodiments of the invention. In each Figure light from an arc lamp 10 is collimated by a collimator 12 and illuminates the full diameter of an optical fibre preform 14 with a collimated beam of light 16. The preform 14 is supported in a transparent, parallel-sided container 18 of index-matching liquid, and the container is sealed by "O" rings 19 which allow the vertical position of the preform 14 to be altered so that different positions along the preform length can be tested. The container is optionally supported by a stepping table 17 which allows the preform to be scanned through the incident beam.

Referring now to FIG. 1 only, light transmitted by the preform 14 is focused by a high-quality spherical lens 20, such as a photographic camera lens. A modulator 22 is placed in the focal plane of the lens 20, and a single photodiode 24 in the image plane of the lens can be stepped by a stepper-motor driven translation slide 26 along a horizontal axis perpendicular to the cylindrical axis of the preform 14, as indicated by the dotted line. The photodiode 24 and modulator 22 are connected to a Time Interval Counter 28, which, together with the translation system 26, is in turn connected to a microprocessor 29 which supplies a display unit 30.

Referring now to FIG. 3, a ray of light entering the preform 14 at position y from the optical axis is deviated by an angle $\Phi$ as shown, and, if the transmitted light is viewed in a plane normal to the incident beam, the intensity distribution in the direction perpendicular to the cylindrical axis of the preform is related to the radial refractive index profile of the preform. Now if a lens 20 is placed in the transmitted beam, then in the focal plane of the lens (sometimes known as the Fourier transform plane) the linear distance $\omega$ of any beam from the optical axis is proportional to the angle of incidence of the beam on the lens, i.e. to the angular deviation $\Phi$ of the beam, provided the angle is small. The relationship is given by:

$$\omega = f \tan \Phi \quad (1)$$

where f is the focal length of the lens and $\Phi$ is the angle of deviation. Thus for small values of $\Phi$, there is in the focal plane a linear distribution of angles $\Phi$ along the $\omega$ axis.

If the illuminating beam is very narrow, as in Chu's method (see above) it can be regarded as a single ray and the value of $\Phi$ for each radial position of the input beam with respect to the preform can be measured directly. If, however, a beam of width at least equal to the preform width is used, a method of isolating individual rays and ascertaining their associated deflection angle is required. If observations are made in an image plane on which the preform is focused by the lens 20, then for a known co-ordinate position y', corresponding to ray position y in the preform, the associated deflection angle $\Phi$ must be determined. The two major embodiments according to the present invention relate to two different methods of achieving this.

In the temporal filtering method illustrated in FIG. 1, suppose the modulator 22 is a constant speed rotary chopper of conventional type with the mark-space ratio radially invariant as shown in FIG. 5, i.e. the blades are radial and straight-edged, and the axis of rotation lies parallel to the optical axis but displaced from it in a direction parallel to the cylindrical axis of the preform. Each blade is thus arranged to sweep the focal plane along the direction in which the various angles deflected by the preform are dispersed by the lens 20, with the relation given in equation (1) above. At each position of the photodiode 24, i.e. for each value of co-ordinate y' in the image plane, movement of the rotary chopper first allows illumination of the photodiode, then as the next blade passes illumination is cut off, so that the diode output is a series of square pulses. The moment in time at which the light is cut on or off depends upon the distance $\omega$ (FIG. 1) from the optic axis (and hence angle $\Phi$ from equation (1)) that a particular ray traverses the focal plane, since the blade progressively sweeps in this direction. Thus the variation in phase of the signal observed by the photodiode at various positions in the image plane relative to a fixed time reference provides a measure of the deflection function, from which the index profile can be computed.

In practice the fixed time-reference is provided by a static photodiode and light source fixed to the body of the chopper at position 22 as is conventional for the provision of a reference signal in light-chopping applications. The time reference is used to provide a START signal to the Time Interval Counter 28, corresponding to a known position of the chopper blade in space, and termination of illumination of the photodiode 24 provides a STOP signal to define pulse length for each value of y'. The microprocessor then calculates the angle $\Phi$ for each y and computes the radial refractive index distribution n(r) of the preform from the deflection function $\Phi$(y) by application of the transform:

$$n(r) = n_o \left[ 1 - \frac{1}{\pi} \int_r^a \tilde{\Phi}(y) (y^2 - r^2)^{-\frac{1}{2}} dy \right] \quad (2)$$

where $n_o = n(a)$, the index of the index matching fluid, r is the radial co-ordinate, a is the radial co-ordinate of the scan starting-point and must be larger than the radius of the preform, and $\tilde{\Phi}$ is related to $\Phi$ by Snell's law, i.e.

$$\tilde{\Phi} = \sin^{-1}\left(\frac{1}{n_o}\sin\Phi\right)$$

The index profile n(r) is displayed on the display unit 30.

The experimental configuration for temporal coding utilising a sweep orthogonal to that described above, i.e. in a direction parallel to the preform axis, is similar to that shown in FIG. 1 but omits the Time Interval Counter 28 and does not require a reference signal. The modulator 22 is a rotary chopper blade chosen to have a mark-space ratio which varies with radial position and the chopper axis of rotation is arranged such that a different mark-space ratio pertains for each ray position $\omega$ in FIG. 1. The chopper is illustrated in FIG. 6. The rays are thus encoded with a certain mark-space ratio depending on the distance $\omega$ from the optic axis (and hence angle $\Phi$ from equation (1)) at which they traverse the focal plane. At each position y' of the photodiode 24 the associated deflection angle $\Phi$ can be found by observation of the signal mark-space ratio, normally measured by applying a low-pass filter and obtaining the average value. Alternatively a Timer/Counter may be used. The microprocessor 29 then relates the mark-space ratio to the deflection angle $\Phi$ for each y and computes the index profile using the transform given in equation (2).

Chopper blades which have a radial mark-space ratio variation may be constructed with straight edges which do not pass through the centre of rotation i.e. non-radial edges, or with curved blades such as given by sections of a linear spiral as shown in FIG. 6. The latter gives a convenient linear variation of mark-space ratio with radial positions.

It is an advantage of the temporal filtering methods that determination of the profile depends on the measurement of a relative pulse phase or a mark-space ratio, and is independent of intensity distribution in the illuminating beam.

The experimental arrangement for spatial modulation in the form of intensity encoding is again similar to that of FIG. 1, but omits the Time Interval Counter, and the modulator 22 comprises a static filter having a transmission factor which varies in a direction defined by $\omega$ in FIG. 3. The rays are thus encoded in intensity depending on the distance $\omega$ from the optic axis at which they traverse the focal plane. Measurement by the photocell 24 of the intensity at position y' in the image plane permits the relationship between position y of a ray impinging on the preform and its associated deflection angle $\Phi$ to be determined. The microprocessor 29 relates the intensity to the deflection angle and computes the index profile using the transform given in equation (2). This arrangement is susceptible to fluctuations in the intensity of illumination.

Referring now to FIG. 2, for an alternative method of spatial modulation in the Fourier plane light transmitted by the preform 14 is focused by a cylindrical lens 32 having its axis parallel to the cylindrical axis of the preform 14 onto the focal plane in which a straight knife edge 34 is arranged. Beyond the knife edge and in the image plane is a diode array 36 connected to a microprocessor 29 and display unit 30. The optical arrangement is illustrated in detail in FIG. 4.

For a ray emerging from the preform at angle $\Phi$, in a plane transverse to the cylindrical axis the effect of the cylindrical lens is to image the ray at a distance $\omega$ from the central axis in the focal or Fourier plane of the lens. The lens does not provide any focusing effect in a direction parallel to its cylindrical axis, but provides only a lateral spread of rays where:

$$\omega = f \tan \Phi \quad (1)$$

for small angles as before. With a straight knife edge 34 placed in the focal plane and making an angle $\alpha$ with the horizontal axis in the plane, and considering a ray with deflection angle $\Phi$, whether or not the ray passes or is intercepted by the knife edge depends on its vertical co-ordinate $\nu$ in the focal plane. The condition for transmission is:

$$\nu \geq \omega \tan \alpha \quad (3)$$

The effect of the spatial filter is to produce a shadowgraph in the image plane 38 at distance d from the focal plane; if the co-ordinates of the plane are x' and y', then by noting that $x = \nu = x'$, and $$y' = \left(\frac{d}{f} - 1\right) y,$$

where d is the distance from the focal plane to the image plane, then by substituting equation (2) into equation (1):

$$\Phi(y) = \tan^{-1}\left[\frac{x'(y')}{f \tan \alpha}\right] \quad (4)$$

Thus for small deflection angles, x' is proportional to $\Phi$ and the shadow boundary x'(y') has the geometrical form of the deflection function of the preform.

Further, the relationship between $\Phi$ and x' depends on the tilt angle $\alpha$ of the knife edge; increasing this angle increases the value of x' and thus "magnifies" the shadowgraph.

The shadow boundary, which is the deflection function, can be measured by a diode array, reference 36 in FIG. 2, which can either be a two dimensional array, or can be a linear array which is stepped across the image plane. The outputs of the diodes are processed to reveal the geometrical co-ordinates of the shadow edge, and therefore the deflection function, and the microprocessor 29 calculates the radial refractive index distribution n(r) of the preform from the deflection function by application of the transform given in equation 2.

It is an advantage of the arrangement using knife-edge filtering that determination of the profile depends on the geometrical measurement of the shadow boundary, is a linear relationship, is easily visible, and is independent of variations in the intensity of the illuminating beam 16. A disadvantage is that a cylindrical lens is required; such lenses may not be of high optical quality.

The invention has been described with reference to use of a powerful white light source. It may in some circumstances be preferable to use a source of restricted wavelength range; a laser may be used if spurious interference patterns can be eliminated or if the slight dispersion present with white light cannot be tolerated.

The invention can also be applied to an optical fibre, since the distribution of angles in the lens focal-plane is similar to that of the parent preform. Thus the temporal or spatial filter used to encode the fibre can be similar to that used for the preform. It will, however, be necessary to provide additional optical magnifying means so that the size of the image is sufficiently large for accurate measurement to be possible.

In a modified use, the invention can be applied to an object which intentionally does not have circular symmetry. The refractive index profile can be determined along a plurality of different radii centred on the same point. A three dimensional profile of the object can then be constructed.

Many variations of the described apparatus are possible. For example, instead of scanning the detector system, the illuminating beam can be angularly swept, or the knife edge in FIG. 2 can be scanned.

The resolution of the system depends on the quality of the lens used, and, as stated above, the lens must have a numerical aperture sufficient to accept a ray of light with the largest deflection imposed by the test object.

We claim:

1. A method of sensing the optical deflection function of an approximately cylindrical object comprises:
   illuminating the object over its width to be tested with a collimated beam of light;
   sensing the light transmitted by the object so that in the focal plane the distance of transmitted light from the optical axis in a direction perpendicular to the cylindrical axis of the object is linearly proportional to the angle through which light has been deviated by the object;
   passing the focused light through a modulator to cause a parameter of the light by means of a modulator to vary as a function of said distance; and
   receiving the modulated light in an image plane, and measuring said parameter at a plurality of positions in said image plane, whereby the deflection function of the object can be derived.

2. A method according to claim 1 in which the focused light is modulated so that a said parameter of the light varies in a direction parallel to said direction.

3. A method according to claim 2 in which the said parameter is the intensity of the light.

4. A method according to claim 2 in which the said parameter is the shadow boundary of light in the image plane.

5. A method according to claim 1 including causing a temporal variation of a parameter of the light in a direction parallel to said direction.

6. A method according to claim 5 in which said parameter is the pulse width of pulses of light.

7. Apparatus for sensing the optical deflection function of an approximately cylindrical object comprising in series, optical focusing means (20), optical modulating means (22), optical receiving means (24), and calculating means (29), arranged so that when the object is illuminated by a beam of collimated light, the receiving means receives at a plurality of positions in an image plane light having a parameter which is modulated by said optical modulating means and which varies along a direction perpendicular to the optical axis of the apparatus and to the cylindrical axis of the object, said varying parameter indicating the angle through which light has been deviated by the object, and the calculating means calculating from said varying parameter the optical deflection function of the object.

8. Apparatus according to claim 7 in which the optical modulating means (22) temporally modulates light received from the object through the focusing means.

9. Apparatus according to claim 7 in which the optical modulating means (34) spatially modulates the intensity of light received from the object through the focusing means.

10. Apparatus according to claim 9 in which the optical modulating means comprises a filter (22) having a transmittance which varies in a direction perpendicular to the cylindrical axis of the object and the direction perpendicular to that axis and to the optical axis, and the optical receiving means (36) is sensitive to the intensity of light incident on it.

11. Apparatus according to claim 9 in which the optical modulating means comprises on opaque screen (34) having an edge of known form arranged in a plane perpendicular to the optical axis of the apparatus and at a known angle to both the cylindrical axis of the object and the direction perpendicular to the cylindrical axis and to the optical axis, whereby in an image plane the shadow of the edge has a form related to the deflection function of the object.

12. Apparatus according to any one of claims 7 to 11 in which the calculating means (29) is further arranged to mathematically transform the optical deflection function so as to derive the refractive index profile of the object.

13. Apparatus for sensing the optical deflection function of an approximately cylindrical object comprising, in series, optical focusing means, optical modulating means, optical receiving means, and calculating means, arranged so that when the object is illuminated by a beam of collimated light, the receiving means receives at a plurality of positions in an image plane light having a parameter which is modulated by said optical modulating means and which varies along a direction perpendicular to the optical axis of the apparatus and to the cylindrical axis of the object, said varying parameter indicating the angle through which light has been deviated by the object, and a calculating means calculating from said varying parameter the optical deflection function of the object, with said optical modulating means temporally modulating light received from the object through the focusing means, said optical modulating means comprising an opaque shutter arranged to repeatedly pass along said direction perpendicular to the cylindrical axis and the optical axis at a constant mark-space ratio, and the optical receiving means being sensitive to the phase of pulses of modulated light.

14. Apparatus for sensing the optical deflection function of an approximately cylindrical object comprising, in series, optical focusing means, optical modulating means, optical receiving means, and calculating means, arranged so that when the object is illuminated by a beam of collimated light, the receiving means receives at a plurality of positions in an image plane, light having a parameter which is modulated by said optical modulating means and which varies along a direction perpendicular to the optical axis of the apparatus and to the cylindrical axis of the object, said varying parameter indicating the angle through which light has been deviated by the object, and the calculating means calculating from said varying parameter the optical deflection function of the object, the optical modulating means temporally modulating light received from the object through the focusing means, said optical modulating means comprising an opaque shutter arranged to repeatedly pass in a direction parallel to the cylindrical axis of the object at a mark-space ratio which is dependent on distance along said direction perpendicular to the cylindrical axis and the optical axis, and the optical receiving means being sensitive to the mark-space ratio of the pulses of modulated light.

15. A method of sensing the optical deflection function of an approximately cylindrical object comprising:
illuminating the object over its width to be tested with a collimated beam of light;
focusing the light transmitted by the object so that in the focal plane the distance of transmitted light from the optical axis in a direction perpendicular to the cylindrical axis of the object is linearly proportional to the angle through which light has been deviated by the object;
passing the focused light through a modulator to cause a parameter of the light by means of a detector to vary as a function of said distance; and
receiving the modulated light in an image plane and measuring said parameter at a plurality of positions in said image plane, whereby the deflection function of the object can be derived;
said method further including causing a temporal variation of a parameter of the light in a direction parallel to said direction with said parameter being the pulse phase of pulses of light.

* * * * *